(12) United States Patent
Gawtrey et al.

(10) Patent No.: US 6,824,765 B2
(45) Date of Patent: Nov. 30, 2004

(54) USE OF PARTICULAR AMINOSILICONES AS POST-TREATMENT OF PROCESSES FOR COLORING KERATIN FIBERS WITH DIRECT DYES OR WITH OXIDATION DYES

(75) Inventors: Jonathan Gawtrey, Boulogne (FR); Serge Restle, Saint-Prix (FR); Priscille Devin-Baudoin, Vanves (FR); Anne Sabbagh, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/290,373

(22) Filed: Nov. 8, 2002

(65) Prior Publication Data

US 2004/0010863 A1 Jan. 22, 2004

(30) Foreign Application Priority Data

Nov. 8, 2001 (FR) .......................................... 01 14475

(51) Int. Cl.⁷ ................................................ A61K 7/00
(52) U.S. Cl. .................... 424/70.1; 424/70.2; 424/70.6; 424/70.11; 424/70.12; 424/70.19; 424/70.122; 8/405; 8/406; 8/410; 8/421; 8/581; 8/632
(58) Field of Search ............................... 424/70.1, 70.2, 424/70.6, 70.11, 70.12, 70.19, 70.122; 8/405, 406, 410, 421, 581, 632

(56) References Cited

U.S. PATENT DOCUMENTS 4,710,314 A * 12/1987 Madrange et al. .......... 510/122

* cited by examiner

Primary Examiner—Brian P. Mruk
Assistant Examiner—Eisa Elhio
(74) Attorney, Agent, or Firm—Finnegan, Henderson, Farabow, Garrett & Dunner L.L.P.

(57) ABSTRACT

A process for post-treating keratin fibres, after a process for coloring with at least one dye chosen from direct dyes and oxidation dyes, by applying a composition comprising at least one aminosilicone.

Process for coloring, with direct dyes or with oxidation dyes, keratin fibres using the composition.

64 Claims, No Drawings

USE OF PARTICULAR AMINOSILICONES AS POST-TREATMENT OF PROCESSES FOR COLORING KERATIN FIBERS WITH DIRECT DYES OR WITH OXIDATION DYES

This disclosure relates to the use, as a post-treatment of a process for coloring, with direct dyes or with oxidation dyes, human keratin fibres, such as hair, of a composition comprising at least one particular aminosilicone.

This disclosure also relates to a process for coloring, with direct dyes or with oxidation dyes, human keratin fibres such as hair, comprising a post-treatment with a composition comprising at least one particular aminosilicone.

Two main types of processes for coloring keratin fibres exist: "direct dyeing" using, in the presence or absence of oxidizing agents, direct dyes and/or pigments which are colored molecules, giving the fibres a temporary color that fades out after shampooing a few times; and "oxidation dyeing" using oxidation dye precursors and an oxidizing agent, which give the fibres a more resistant color than that obtained with the previous type of dyeing.

The use of an oxidizing agent generally results in a certain level of degradation of the keratin fibre.

There is currently a very marked trend towards increasing the frequency of shampooing, which is reflected by a more substantial degradation of the dyeing results between two applications.

There is thus a need to improve the resistance of colorations with direct dyes or with oxidation dyes, for example, with respect to shampooing.

The inventors have discovered that the use, as a post-treatment on human keratin fibres such as hair, of a composition comprising at least one particular aminosilicone, allows at least one of the foregoing problems to be solved. This discovery forms at least a portion of the basis for at least one embodiment disclosed herein.

In addition, this post-treatment may improve the condition of the fibre, for example, in the case of a prior coloration in the presence of an oxidizing agent.

As used herein, the phrase "improvement in the condition of the fibre" means a reduction in the porosity or the alkaline solubility of the fibre and an improvement in at least one cosmetic property such as, for example, the smoothness, softness, and ease of disentangling and styling.

This effect can be remanent, i.e. long-lasting.

The porosity is measured by fixing, at 37° C. and at pH 10, for 2 minutes, 2-nitro-para-phenylenediamine at 0.25% in an ethanol/pH 10 buffer mixture (10/90 volume ratio).

The alkaline solubility corresponds to the loss of mass of a sample of 100 mg of keratin fibres under the action of decinormal sodium hydroxide for 30 minutes at 65° C.

One new embodiment relates to a process for the post-treatment in a process for coloring, with oxidation dyes or with direct dyes, human keratin fibres, such as hair, comprising at least one aminosilicone chosen from formulae (I) and (II), as defined herein.

An embodiment of the process can improve the resistance to shampooing of the said colourations and/or the condition of the fibre after coloration, for example, in the case of coloring with an oxidizing agent. This post-treatment may take place immediately after dyeing and optional rinsing, or after an interval, and may be performed once only or repeatedly between two colorations.

Another new embodiment relates to a coloring process that comprises applying to human keratin fibres, such as hair, a direct dye composition or oxidation dye composition for a time that is sufficient to develop the color, and following this application, after optionally rinsing, and after optionally drying, with the application of a composition comprising at least one aminosilicone chosen from formulae (I) and (II).

Aminosilicones

The at least one aminosilicone is chosen from formulae (I) and (II):

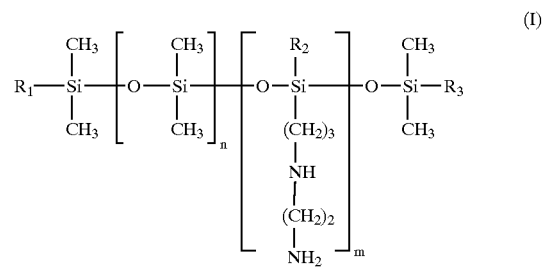

(I)

wherein:
- m and n are chosen from numbers such that the sum (n+m) ranges, for example, from 1 to 1000 and, for example, from 50 to 250 and, in yet another example, from 100 to 200;
- n ranges from 0 to 999 and, for example from 49 to 249 and further, for example, from 125 to 175, and m ranges from 1 to 1000, for example, from 1 to 10 and further, for example, from 1 to 5;
- $R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals.

For example, the alkoxy radical may be a methoxy radical.

The hydroxyl/alkoxy molar ratio may range from 0.2:1 to 0.4:1, for example, from 0.25:1 to 0.35:1 and further, for example, 0.3:1.

The at least one aminosilicone of formula (I) may have a weight-average molecular mass ranging from 2000 to 1 000 000, for example from 3500 to 200 000.

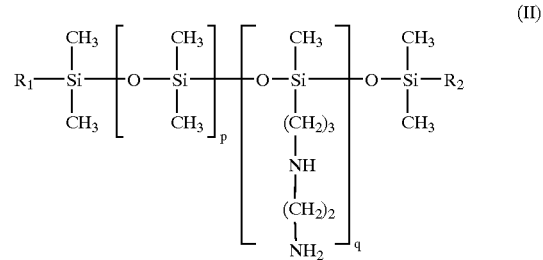

(II)

wherein:
- p and q are chosen from numbers such that the sum (p+q) ranges from 1 to 1000, for example from 50 to 350 and further, for example, from 150 to 250;
- p is chosen from a number ranging from 0 to 999, for example from 49 to 349 and further, for example, from 159 to 239, and q is chosen from a number ranging from 1 to 1000, for example from 1 to 10 and further, for example, from 1 to 5;
- $R_1$ and $R_2$, which are different, are chosen from a hydroxyl radical and C1–C4 alkoxy radicals, with at least one of the radicals $R_1$ and $R_2$ being an alkoxy radical.

For example, the alkoxy radical may be a methoxy radical.

The hydroxyl/alkoxy molar ratio may range, for example, from 1:0.8 to 1:1.1, and further, for example, from 1:0.9 to 1:1 and, for yet another example, may be 1:0.95.

The at least one aminosilicone of formula (II) has a weight-average molecular mass ranging, for example, from 2000 to 200 000, for example from 5000 to 100 000 and further, for example, from 10 000 to 50 000.

The weight-average molecular masses of the at least one aminosilicone is measured by Gel Permeation Chromatography (GPC) at room temperature, as a polystyrene equivalent. The columns used are styragel $\mu$ columns. The eluent is THF, and the flow rate is 1 ml/minute. 200 $\mu$l of a solution at 0.5% by weight of silicone in THF are injected. The detection is performed by refractometry and UV-metry.

The post-treatment compositions comprising at least one aminosilicone of formulae (I) and (II) may include at least one additional aminosilicone, whose formula is different from formulae (I) and (II).

A product comprising at least one aminosilicone of structure (I) is sold by the company Wacker under the name Belsil ADM 652®.

Products comprising at least one aminosilicone of structure (II) are sold by the company Wacker under the names Fluid WR 1300® and Belsil ADM 6057®.

When at least one aminosilicone is used, one embodiment involves using the at least one aminosilicone in the form of an oil-in-water emulsion. The oil-in-water emulsion may comprise at least one surfactant. The at least one surfactant may be of any nature, for example cationic and/or nonionic.

The silicone particles in the emulsion may have a mean size ranging from 3 to 500 nanometres.

For example, for the at least one aminosilicone of formula (II), particles in microemulsions may range in size from 5 to 60 nanometres and, for example, from 10 to 50 nanometres. Such particle sizes are measured with a laser granulometer.

For example, a microemulsion of the at least one aminosilicone of formula (II), sold under the name Finish CT 96 E® or SLM 28020® by the company Wacker may be used.

The at least one aminosilicone chosen from formulae (I) and (II) may be chosen such that the contact angle with water of a hair treated with a composition comprising 2% AM (active materials) of the at least one aminosilicone ranges from 90 to 180°, for example, 90 to 130°.

The composition comprising the at least one aminosilicone chosen from formula (I) and (II) may be chosen such that the contact angle of a hair treated with the composition ranges from 90 to 180°; for example, from 90 to 130°.

The contact angle measurement is based on immersing a hair in distilled water. The measurement is derived from evaluating the force exerted by the water on the hair during its immersion in distilled water and the force exerted during its removal. The forces are directly linked to the contact angle $\theta$ between the water and the surface of the hair. The hair is hydrophilic when the angle $\theta$ ranges from 0 to less than 90°, and hydrophobic when the angle ranges from 90° to 180°.

The test is carried out with locks of natural hair that have been bleached under the same conditions and then washed.

Each 1 gram lock is placed in a crystallizing dish 75 mm in diameter and then covered uniformly with 5 ml of the test formulation. The lock is left for 15 minutes at room temperature and then rinsed for 30 seconds. The drained lock is left in the open air until it is completely dry.

For each evaluation, 10 hairs that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of each hair is measured by means of observation by microscope.

The mean wettability force on 10 hairs and the cross section of the analysed hairs make it possible to obtain the contact angle of the hair on the water, according to the formula:

$$F = P * \gamma lv * \cos \theta$$

where F is the wettability force expressed in newtons, P is the perimeter of the hair in metres, $\gamma$lv is the liquid/water vapour interface tension in J/m$^2$, and $\theta$ is the contact angle.

For example, the product SLM 28020® from Wacker at 12% in water (i.e. 2% aminosilicone) gives a contact angle of 93° according to the test indicated above.

Another embodiment comprises the use of at least one aminosilicone in the post-treatment composition in an amount ranging, for example, from 0.01% to 20% by weight relative to the total weight of the composition, and further, for example, from 0.1% to 15% by weight relative to the total weight of the composition and, for yet further, for example, from 0.5% to 10% by weight relative to the total weight of the composition.

The post-treatment composition may comprise any ingredient conventionally used in cosmetics, such as in the field of haircare. For example, it may comprise at least one additional surfactant and/or polymer. These surfactants and polymers may be chosen from nonionic, cationic, anionic, and amphoteric surfactants and polymers. Among the additional polymers, aminosilicones, other than the at least one aminosilicone of formulae (I) and (II) disclosed herein, may be used.

The post-treatment composition may have a pH ranging from 2 to 11, for example from 4 to 9.

The post-treatment composition may be in various forms, for example, lotions, gels, creams, shampoos, sticks, mousses and sprays. For some of these forms, it may be packaged in a pump-dispenser bottle or in an aerosol container. In the case of an aerosol, the composition may be combined with a propellant that may be, for example, an alkane or a mixture of alkane, dimethyl ether, nitrogen, nitrous oxide, carbon dioxide and haloalkanes, and also mixtures thereof.

In one new embodiment, the post-treatment composition may be in shampoo form.

When the post-treatment composition is in shampoo form, the composition may comprise at least one surfactant, for example an anionic surfactant. For example, the post-treatment composition may comprise a mixture of surfactants, comprising at least one anionic surfactant, and at least one other surfactant, chosen from nonionic and amphoteric surfactants.

As mentioned above, the post-treatment composition may be applied immediately after coloration, or after an interval. The expression "after an interval" means an application performed a few hours, one day or several days (from 1 to 60 days) after the coloration.

In another new embodiment, several applications may be carried out between two colorations.

The number of applications between two colorations may range, for example, from 1 to 60, and further, for example, from 2 to 30.

The post-treatment composition may be used in rinse-out or leave-in mode, i.e. its application may or may not be followed by a rinsing operation.

In the first case, the acting time of the post-treatment composition may be, for example, from a few seconds to 60 minutes and further, for example, from 30 seconds to 15 minutes.

The application temperature of the post-treatment composition may range, for example, from 10° C. to 70° C. Further, for example, the application temperature may range from 10° C. to 60° C. and, for yet another example, the application temperature may be at room temperature.

In the case of colorations with direct dyes (in the presence or absence of oxidizing agents), the dye compositions comprise at least one dye chosen from neutral, acidic and cationic nitrobenzene direct dyes, neutral, acidic and cationic azo and methine direct dyes, neutral, acidic and cationic quinone direct dyes, for example, anthraquinone direct dyes, azine direct dyes, triarylmethane direct dyes, indoamine direct dyes, natural direct dyes, and mixtures thereof.

In the case of colorations with oxidation dyes, the dye compositions may comprise at least one oxidation base.

The at least one oxidation base may be chosen from those conventionally used in oxidation dyeing, for example ortho-phenylenediamines, para-phenylenediamines, double bases, ortho-aminophenols, para-aminophenols, heterocyclic bases, and their acid addition salts.

The oxidation dye compositions may also comprise at least one coupler.

Representatives of the at least one coupler may include, for example, meta-phenylenediamines, meta-aminophenols, meta-diphenols, mono- and polyhydroxylated aminophenols, sesamol and its derivatives, and heterocyclic compounds such as, for example, indole couplers, indoline couplers, pyridine couplers, and their acid addition salts.

The at least one oxidizing agent may be chosen, for example, from hydrogen peroxide, urea peroxide, alkali metal bromates, ferricyanides, and persalts such as, for example, perborates and persulphates. At least one redox enzyme such as, for example, laccases, peroxidases and 2-electron oxidoreductases (such as uricase) may also be used as an oxidizing agent, where appropriate in the presence of the respective donor or cofactor.

Examples of new embodiments described herein are indicated below without, however, being limiting in nature.

EXAMPLES

The five post-treatment compositions A, B, C, D and E below were prepared. (expressed as grams of Active Material (AM))

| Composition A | |
|---|---|
| Polydimethylsiloxane of formula (I), sold under the name Belsil ADM 652 ® by the company Wacker | 2.0 |
| Solvent qs | 100 |
| Composition B | |
| Polydimethylsiloxane of formula (II) sold under the name Belsil ADM 6057 ® by the company Wacker | 2.0 |
| Demineralized water qs | 100 |
| Composition C | |
| Polydimethylsiloxane of formula (II) sold under the name SLM 28020 ® by the company Wacker | 2.0 |
| Demineralized water qs | 100 |
| Composition D | |
| Sodium lauryl ether sulphate containing 2.2 mol of ethylene oxide | 7 |
| Cocoylbetaine | 2.5 |
| Glycol distearate | 1.5 |
| Polydimethylsiloxane of formula (II) sold under the name SLM 28020 ® by the company Wacker | 1.5 |
| Hydroxyethylcellulose quaternized with 2,3-epoxypropyltrimethylammonium chloride, sold under the brand name Ucare Polymer JR-400 ® by Union Carbide | 0.4 |
| Acrylic polymer as an emulsion sold under the brand name Aqua SF1 ® by Noveon | 0.8 |
| Preserving agents | qs |
| pH agents qs | pH 5 |
| Demineralized water qs | 100 |
| Composition E | |
| Sodium lauryl ether sulphate containing 2.2 mol of ethylene oxide | 7 |
| Cocoylbetaine | 2.5 |
| Glycol distearate | 1.5 |
| Polydimethylsiloxane of viscosity 60 000 mm$^2$/s, sold under the name Dow Corning 200 Fluid ® by Dow Corning | 1.0 |
| Polydimethylsiloxane of formula (I) sold under the name Belsil ADM 652 ® by the company Wacker | 2 |
| Hydroxyethylcellulose quaternized with 2,3-epoxypropyltrimethylammonium chloride, sold under the brand name Ucare Polymer JR-400 ® by Union Carbide | 0.4 |
| Acrylic polymer as an emulsion sold under the brand name Aqua SF1 ® by Noveon | 0.8 |
| Preserving agents | qs |
| pH agents qs | pH 5 |
| Demineralized water qs | 100 |

Compositions A and B were applied for two minutes to locks of moderately bleached hair dyed with the commercial oxidation dye Majirouge®, shade 7.40.

After rinsing and drying, five standard shampoo washes were carried out on these locks.

For comparative purposes, locks dyed under the same conditions, and subjected to the same shampooing protocol, were subjected to a post-treatment with demineralized water instead of post-treatment with compositions A and B.

Results: the degradation of the color (DE in the L*a*b* system) relative to an unshampooed lock was evaluated in comparison with the case in which the post-treatment according to the invention was replaced with a post-treatment with demineralized water.

The following results were obtained:

| Composition A | DE = 6.0 |
|---|---|
| Composition B | DE = 5.7 |
| Placebo | DE = 8.0 |

The lower the value of DE, the less the degradation. Compositions A and B used as post-treatment after coloration with the oxidation dye Majirouge® 7.40 thus protected against the degradation caused by shampooing.

Moreover, the condition of the hair fibres was satisfactory.

Composition C was applied, without subsequent rinsing, to locks of natural hair containing 90% white hairs colored with the oxidation dye Majirouge® shade 6.64. After drying, eight DOP shampoo washes were carried out.

Results: the degradation of the color (DE in the L*a*b* system) relative to an unshampooed lock was evaluated in comparison with the case in which no post-treatment according to the invention was carried out.

The following results were obtained:

| | |
|---|---|
| Composition C | DE = 4.6 |
| Placebo | DE = 7.3 |

The lower the value of DE, the less the degradation. Composition C used as post-treatment after coloration with the oxidation dye Majirouge® 6.64 thus protected against the degradation caused by shampooing.

Moreover, the condition of the hair fibres was satisfactory.

Compositions D and E were used as care shampoos on colorations with oxidation dyes or with direct dyes. The degradations of the initial shades were less than in the case where a standard care shampoo was used (without the aminosilicone of the invention). The condition of the hair fibres was judged to be better.

What is claimed is:

1. A process for post-treating keratin fibres that have been subjected to a process for coloring with at least one dye chosen from direct dyes and oxidation dyes, comprising applying a post-treatment composition comprising at least one aminosilicone chosen from formulae (I) and (II):

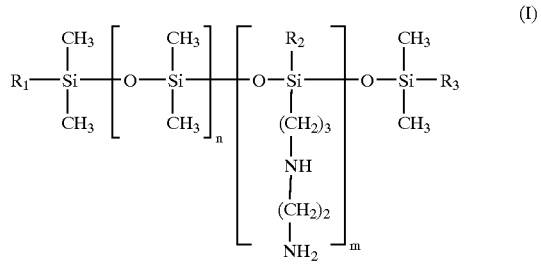

(I)

wherein:
m and n are numbers with a sum (n+m) ranging from 1 to 1000,
n is a number ranging from 0 to 999, and m is a number from 1 to 1000;
$R_1$, $R_2$ and $R_3$, which may be identical or different, are chosen from a hydroxyl radical and C1–C4 alkoxy radicals, at least one of the radicals $R_1$ to $R_3$ being an alkoxy radical; and

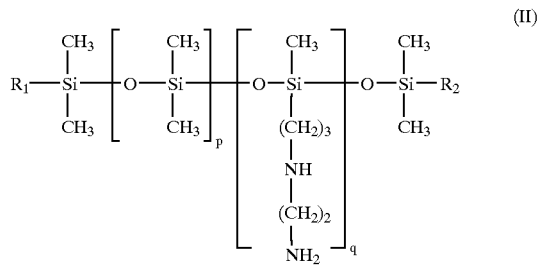

(II)

wherein:
p and q are numbers with a sum (p+q) ranging from 1 to 1000,
p is a number ranging from 0 to 999, and q is a number ranging from 1 to 1000; and
$R_1$ and $R_2$, which are different, are chosen from a hydroxyl radical and C1–C4 alkoxy radicals, at least one of the radicals $R_1$ and $R_2$ being an alkoxy radical.

2. The process according to claim 1, wherein the keratin fibres are hair.
3. The process according to claim 1, wherein in formula (I), the sum (m+n) ranges from 50 to 250.
4. The process according to claim 1, wherein in formula (I), the sum (m+n) ranges from 100 to 200.
5. The process according to claim 1, wherein in formula (I), n ranges from 49 to 249.
6. The process according to claim 1, wherein in formula (I), n ranges from 125 to 175.
7. The process according to claim 1, wherein in formula (I), m ranges from 1 to 10.
8. The process according to claim 1, wherein in formula (I), m ranges from 1 to 5.
9. The process according to claim 1, wherein in formula (II), the sum (p+q) ranges from 50 to 350.
10. The process according to claim 1, wherein in formula (II), the sum (p+q) ranges from 150 to 250.
11. The process according to claim 1, wherein in formula (II), p ranges from 49 to 349.
12. The process according to claim 1, wherein in formula (II), p ranges from 159 to 239.
13. The process according to claim 1, wherein in formula (II), q ranges from 1 to 10.
14. The process according to claim 1, wherein in formula (II), q ranges from 1 to 5.
15. The process according to claim 1, wherein the $C_1$–$C_4$ alkoxy radical is a methoxy radical.
16. The process according to claim 1, wherein the at least one aminosilicone is chosen from formula (I) and has a hydroxyl/alkoxy molar ratio ranging from 0.2:1 to 0.4:1.
17. The process according to claim 1, wherein the at least one aminosilicone is chosen from formula (I) and has a hydroxyl/alkoxy molar ratio ranging from 0.25:1 to 0.35:1.
18. The process according to claim 1, wherein the at least one aminosilicone is chosen from formula (I) and has a hydroxyl/alkoxy molar ratio of 0.3:1.
19. The process according to claim 1, wherein the at least one aminosilicone is chosen from formula (II) and has a hydroxyl/alkoxy molar ratio ranging from 1:0.8 to 1:1.1.
20. The process according to claim 1, wherein the at least one aminosilicone is chosen from formula (II) and has a hydroxyl/alkoxy molar ratio ranging from 1:0.9 to 1:1.
21. The process according to claim 1, wherein the at least one aminosilicone is chosen from formula (II) and has a hydroxyl/alkoxy molar ratio of 1:0.95.
22. The process according to claim 1, wherein the at least one aminosilicone is chosen from formula (I) and has a weight-average molecular mass ranging from 2000 to 1 000 000.
23. The process according to claim 1, wherein the at least one aminosilicone is chosen from formula (I) and has a weight-average molecular mass ranging from 3500 to 200 000.
24. The process according to claim 1, wherein the at least one aminosilicone is chosen from formula (II) and has a weight-average molecular mass ranging from 2000 to 200 000.
25. The process according to claim 1, wherein the at least one aminosilicone is chosen from formula (II) and has a weight-average molecular mass ranging from 5000 to 100 000.
26. The process according to claim 1, wherein the at least one aminosilicone is chosen from formula (II) and has a weight-average molecular mass ranging from 10 000 to 50 000.
27. The process according to claim 1, wherein the at least one aminosilicone is in the form of an oil-in-water emulsion and further comprises at least one surfactant.

28. The process according to claim 27, wherein the at least one surfactant is chosen from cationic and nonionic surfactants.

29. The process according to claim 27, wherein the particle size of the at least one aminosilicone in the emulsion ranges from 3 to 500 nanometres.

30. The process according to claim 29, wherein the particle size of the at least one aminosilicone in the emulsion ranges from 5 to 60 nanometres.

31. The process according to claim 30, wherein the particle size of the at least one aminosilicone in the emulsion ranges from 10 to 50 nanometres.

32. The process according to claim 1, wherein the at least one aminosilicone is chosen such that a contact angle with water of hair treated with a composition comprising 2% AM (active materials) of said at least one aminosilicone ranges from 90 to 180°.

33. The process according to claim 32, wherein the at least one aminosilicone is chosen such that a contact angle with water of hair treated with a composition comprising 2% AM (active materials) of said aminosilicone ranges from 90 to 130°.

34. The process according to claim 1, wherein the composition comprising at least one aminosilicone is chosen such that a contact angle of hair treated with said composition ranges from 90 to 180°.

35. The process according to claim 1, wherein the at least one aminosilicone is present in an amount ranging from 0.01% to 20% by weight, relative to the total weight of the composition.

36. The process according to claim 35, wherein the at least one aminosilicone is present in an amount ranging from 0.1% to 15% by weight, relative to the total weight of the composition.

37. The process according to claim 36, wherein the at least one aminosilicone is present in an amount ranging from 0.5% to 10% by weight, relative to the total weight of the composition.

38. The process according to claim 1, wherein the post-treatment composition is in a form chosen from lotions, gels, creams, shampoos, sticks, mousses and sprays.

39. The process according claim 1, wherein the post-treatment composition is packaged in a form chosen from pump-dispenser bottles and aerosol containers.

40. The process according to claim 39, wherein the post-treatment composition further comprises at least one propellant chosen from alkanes, dimethyl ether, nitrogen, nitrous oxide, carbon dioxide and haloalkanes.

41. The process according to claim 1, wherein the post-treatment composition further comprises at least one surfactant chosen from nonionic, cationic, anionic, and amphoteric surfactants.

42. The process according to claim 41, wherein the post-treatment composition comprises at least one anionic surfactant and at least one additional surfactant chosen from nonionic and amphoteric surfactants.

43. The process according to claim 1, wherein the post-treatment composition comprises at least one additional polymer other than the at least one aminosilicone chosen from formulae (I) and (II).

44. The process according to claim 43, wherein the at least one additional polymer is chosen from nonionic, cationic, anionic and amphoteric polymers.

45. The process according to claim 43, wherein the at least one additional polymer is an aminosilicone different from the at least one aminosilicone chosen from formulae (I) and (II).

46. The process according to claim 1, wherein the post-treatment composition has a pH ranging from 2 to 11.

47. The process according to claim 46, wherein the post-treatment composition has a pH ranging from 4 to 9.

48. The process according to claim 1, wherein the post-treatment composition is effective in improving the resistance of colorations.

49. The process according to claim 1, wherein the post-treatment composition is effective in improving the condition of keratin fibres.

50. The process according to claim 49, wherein the post-treatment composition is effective in improving the condition of fibres after a process for coloration comprising applying at least one oxidizing agent.

51. A process for coloring human keratin fibres, comprising:
(a) applying to the fibres a direct dye composition;
(b) leaving the dye to act for a time that is sufficient to develop the color;
(c) applying to the fibres, after optionally rinsing the fibres, and after optionally drying the fibres, a post-treatment composition comprising at least one aminosilicone chosen from formulae (I) and (II):

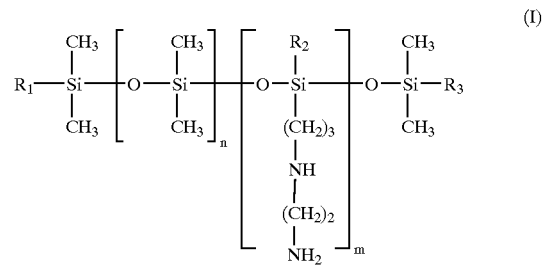

wherein:
m and n are numbers with a sum (n+m) ranging from 1 to 1000,
n is a number ranging from 0 to 999, and m is a number from 1 to 1000;
$R_1$, $R_2$ and $R_3$, which may be identical or different, are chosen from a hydroxyl radical and C1–C4 alkoxy radicals, at least one of the radicals $R_1$ to $R_3$ being an alkoxy radical; and

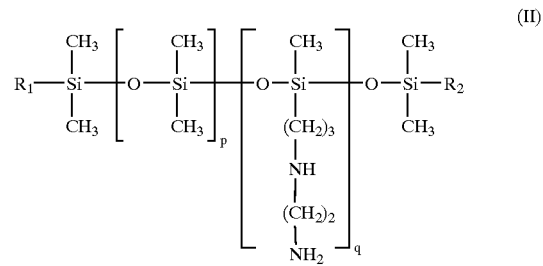

wherein:
p and q are numbers with a sum (p+q) ranging from 1 to 1000,
p is a number ranging from 0 to 999, and q is a number ranging from 1 to 1000; and
$R_1$ and $R_2$, which are different, are chosen from a hydroxyl radical and C1–C4 alkoxy radicals, at least one of the radicals $R_1$ and $R_2$ being an alkoxy radical.

52. The process according to claim 51, wherein the keratin fibres are hair.

53. The process according to claim 51, wherein the post-treatment composition is applied immediately after drying the fibres.

54. The process according to claim 51, wherein the post-treatment composition is applied after an interval.

55. The process according to claim 51, wherein applications of the post-treatment composition are repeated between two colorations.

56. The process according to claim 51, wherein the post-treatment composition is left to act for a period of time ranging from a few seconds to 60 minutes.

57. The process according to claim 51, wherein the post-treatment composition is left to act for a period of time ranging from 30 seconds to 15 minutes.

58. A process for coloring humankeratin fibres, comprising:
   (a) applying to the fibres an oxidation dye composition;
   (b) leaving the oxidation dye composition to act for a time that is sufficient to develop the color;
   (c) applying to the fibres, after optionally rinsing the fibres, and after optionally drying them, a post-treatment composition comprising at least one amino-silicone chosen from formulae (I) and (II):

$$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\left[\underset{\underset{(CH_2)_3-NH-(CH_2)_2-NH_2}{|}}{\overset{\overset{R_2}{|}}{Si}}-O\right]_m-\underset{\underset{CH_3}{|}}{\overset{\overset{CH_3}{|}}{Si}}-R_3 \quad (I)$$

wherein:
   m and n are numbers with a sum (n+m) ranging from 1 to 1000,
   n is a number ranging from 0 to 999, and m is a number from 1 to 1000;
   $R_1$, $R_2$ and $R_3$, which may be identical or different, are chosen from a hydroxyl radical and C1–C4 alkoxy radicals, at least one of the radicals $R_1$ to $R_3$ being an alkoxy radical; and $$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_p-\left[\underset{\underset{(CH_2)_3-NH-(CH_2)_2-NH_2}{|}}{\overset{\overset{CH_3}{|}}{Si}}-O\right]_q-\underset{\underset{CH_3}{|}}{\overset{\overset{CH_3}{|}}{Si}}-R_2 \quad (II)$$

wherein:
   p and q are numbers with a sum (p+q) ranging from 1 to 1000,
   p is a number ranging from 0 to 999, and q is a number ranging from 1 to 1000; and
   $R_1$ and $R_2$, which are different, are chosen from a hydroxyl radical and C1–C4 alkoxy radicals, at least one of the radicals $R_1$ and $R_2$ being an alkoxy radical.

59. The process according to claim 58, wherein the keratin fibres are hair.

60. The process according to claim 58, wherein the post-treatment composition is applied immediately after drying the keratin fibers.

61. The process according to claim 58, wherein the post-treatment composition is applied after an interval.

62. The process according to claim 58, wherein applications of the post-treatment composition are repeated between two colorations.

63. The process according to claim 58, wherein the post-treatment composition is left to act for a period of time ranging from a few seconds to 60 minutes.

64. The process according to claim 58, wherein the post-treatment composition is left to act for a period of time ranging from 30 seconds to 15 minutes.

* * * * *

UNITED STATES PATENT AND TRADEMARK OFFICE
CERTIFICATE OF CORRECTION

PATENT NO. : 6,824,765 B2
DATED : November 30, 2004
INVENTOR(S) : Jonathan Gawtrey et al.

It is certified that error appears in the above-identified patent and that said Letters Patent is hereby corrected as shown below:

Column 9,
Line 42, "according claim" should read -- according to claim --.

Column 11,
Line 14, "humankeratin" should read -- human keratin --.

Signed and Sealed this

Nineteenth Day of April, 2005

JON W. DUDAS
*Director of the United States Patent and Trademark Office*